United States Patent [19]
Witiak et al.

[11] 4,213,999
[45] Jul. 22, 1980

[54] INHIBITION OF LIPOGENESIS

[75] Inventors: Donald T. Witiak, Columbus, Ohio; John B. Carr, Houston, Tex.; Harry J. Mersmann, Modesto, Calif.

[73] Assignee: Shell Oil Company, Houston, Tex.

[21] Appl. No.: 46,593

[22] Filed: Jun. 7, 1979

Related U.S. Application Data

[63] Continuation-in-part of Ser. No. 9,338, Feb. 5, 1979, abandoned, which is a continuation of Ser. No. 904,084, May 8, 1978, abandoned, which is a continuation of Ser. No. 811,647, Jun. 30, 1977, abandoned.

[51] Int. Cl.$^2$ .............................................. A61K 31/34
[52] U.S. Cl. .................................................... 424/285

[58] Field of Search ......................................... 424/285

[56] References Cited

U.S. PATENT DOCUMENTS

| 3,651,094 | 3/1972 | Libis et al. | 424/285 |
| 3,751,430 | 8/1973 | Libis et al. | 424/285 |
| 3,843,797 | 10/1974 | Habicht et al. | 424/285 |
| 3,920,828 | 11/1975 | Scherrer | 424/285 |

Primary Examiner—Stanley J. Friedman

[57] ABSTRACT

Lipogenesis in mammals is inhibited by certain substituted 2-benzofurancarboxylic acid esters, and their 2,3-dihydro counterparts.

1 Claim, No Drawings

INHIBITION OF LIPOGENESIS

This application is a continuation-in-part of application Ser. No. 9,338, filed on Feb. 5, 1979, now abandoned, which was a continuation of application Ser. No. 904,084, filed on May 8, 1978, now abandoned, which was a continuation of application Ser. No. 811,647, filed on June 30, 1977, now abandoned.

DESCRIPTION OF THE INVENTION

It has been found that lipogenesis in mammals is inhibited by certain aliphatic esters of 2-benzofurancarboxylic acids, and the 2,3-dihydro counterparts thereof, all of these esters being described by the formula:

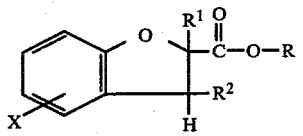

wherein R is alkyl of from one to four carbon atoms or is 2-propenyl, (a) $R^1$ and $R^2$ together represent a second bond between the two carbon atoms, and X is one of the following moieties, bonded to the carbon atom in the indicated position on the molecule:
  (1) 5-benzyl;
  (2) 5-(alkyloxy of from three to six carbon atoms);
  (3) 4-phenoxy;
  (4) 5-benzoyl;
  (5) 5-(4-acetylphenyl);
  (6) 5-(4-acetyloxy)phenyl);
  (7) 5-(4-(1-hydroxyethyl)phenyl);
  (8) 5-(4-acetamidophenyl);
  (9) 5-(4-aminophenyl);
or
(b) $R^1$ and $R^2$ each represents a hydrogen atom, and X is one of the following moieties, bonded to the carbon atom in the indicated position on the molecule:
  (1) 5-phenyl;
  (2) 5-cyclohexyl;
  (3) 5-benzyl;
  (4) 6-phenoxy;
  (5) 4-phenoxy
  (6) 5-(4(1-hydroxyethyl)phenyl);
  (7) 5-(4-chlorophenyl);
  (8) 5-(4-acetamidophenyl).

Chirality exists in the 2,3-dihydro members, hence they can exist in optical isomeric forms. None of the isomers has been separated, nor has the lipogenesis inhibition activity of any of the individual isomers been determined. The 2,3-dihydro species that have been prepared inhibit lipogenesis. Under the circumstances, the invention contemplates the furan subgenus, the 2,3-dihydrofuran subgenus, including the individual isomers of the latter subgenus, as well as mixtures thereof.

The manner in which compounds of Formula I can be prepared is illustrated in the following examples. In each case, the identities of the product, and of the precursor(s) involved, were confirmed by appropriate chemical and spectral analyses.

EXAMPLE 1—Ethyl 5-benzylbenzofuran-2-carboxylate (1)

157 g of sodium hydroxide (50% in water) was added all at once to a stirred mixture of 100 g of p-benzylphenol in 165 ml of ethanol. The mixture was heated to 75°-80° C., and 161.5 g of chloroform was added drop-by-drop to the stirred mixture over a 5-hour period, at 75°-80° C., then was stirred for 2 hours at 75° C. Then 80.8 g of chloroform was added drop-by-drop, at 75°-80° C., and the mixture was stirred for 1 hour at 75° C. This procedure was repeated. The mixture was concentrated under reduced pressure to give a solid residue. The residue was poured into water, and the stirred mixture was acidified with concentrated hydrochloric acid. The aqueous phase was separated, extracted with ether and the extract was concentrated under reduced pressure to give an oil. The oil was extracted with petroleum ether. The extract was concentrated under reduced pressure. The residue was suspended in 150 ml of a saturated solution of sodium bisulfite and the mixture was stirred for 1 hour at room temperature. The liquid was decanted, and the solid was washed with water, stirred with ethanol and the mixture was filtered. The solid was washed with ether, then suspended in 10% sulfuric acid solution. The resulting mixture was stirred for 1½ hours, then extracted with ether. The extract was dried (MgSO₄) and concentrated under reduced pressure to give 5-benzylsalicylaldehyde (1A).

6.9 g of 1A was dissolved in 130 ml of 2-butanone. The solution was heated to reflux and 8.1 g of potassium carbonate was added. Then 7.8 g of diethyl bromomalonate was added, drop-by-drop over a 10-minute period. The mixture was stirred at reflux for 58 hours, then was cooled and filtered. The filtrate was concentrated under reduced pressure to leave an oil, which was poured into water. The mixture was extracted with ether. The extract was washed with 5% sodium hydroxide solution, then with water, dried (MgSO₄), and concentrated under reduced pressure. The residue was recrystallized from methanol and dried over P₂O₅ to give 1, mp: 78°-79° C.

EXAMPLES 2 and 3

By procedures similar to those described in Example 1, the following additional individual species of the benzofuran subclass of the class of compounds defined in Formula I, R being ethyl in both cases, were prepared from known phenols:

| Example No. | Compound No. | R (number indicating) position on ring | m.p. (°C.) |
| --- | --- | --- | --- |
| 2 | 2 | 5-hexyloxy | 50-52 |
| 3 | 3 | 5-benzoyl | 59-61 |

EXAMPLE 4—Ethyl 4-phenoxybenzofuran-2-carboxylate (4)

4, a liquid, was prepared by procedures similar to those described in Example 1, from the precursor salicylaldehyde, prepared as follows:

145.0 g of meta-phenoxyphenol was dissolved in 700 ml of 95% ethanol. 468 g of sodium hydroxide was then added rapidly. The resulting suspension was heated to 70°-80° C. Then 558.7 g of chloroform was added, at such a rate that gentle reflux was maintained; the addition required 10 hours. The mixture then was stirred for 2 hours at 70°-80° C., held at room temperature overnight and filtered. The solid product was dissolved in 1000 ml of water. The solution was acidified to pH=2 with concentrated hydrochloric acid, then was extracted with ether. The ether layer was dried (MgSO₄) and concentrated. The residue was extracted with hot petroleum ether. The extract was dried (Na₂SO₄) and concentrated to give an oil, which was wet column chromatographed, using first at 9/1 v/v mixture, then a 4/1 v/v mixture of petroleum ether and ethyl ether as eluent. The fourth fraction obtained, after removal of the solvents, was identified as 2-hydroxy-6-phenoxybenzaldehyde.

EXAMPLE 5—Ethyl 5-(4-acetylphenyl)benzofuran-2-carboxylate (5)

22 g of p-phenylphenol was dissolved in 95% ethanol; a solution of 40 g of sodium hydroxide in 80 ml of water was rapidly added. The resulting solution was heated to 75°–80° C. and 20 ml of chloroform was added over a one-hour period, the mixture being gently refluxed. The mixture then was stirred for three hours, cooled and the ethanol and excess chloroform were evaporated under reduced pressure. The resulting residue was cooled and poured into cold water. The resulting mixture was acidified by slow addition of hydrochloric acid and extracted with ether. The solvent was evaporated from the extract under reduced pressure, the residue was poured in twice its volume of saturated sodium metabisulfite solution and the mixture was shaken vigorously for forty-five minutes. The resulting semisolid bisulfite addition compound was allowed to stand for one hour, filtered in the dark and washed with small portions of ethanol and ether to remove the phenol. The bisulfite addition compound was decomposed with dilute sulfuric acid, the mixture being warmed on a water-bath for thirty minutes. The cooled mixture was extracted with ether. The extract was dried (Na₂SO₄), and the solvent was evaporated under reduced pressure. The residue was treated with activated charcoal and recrystallized from ethanol/water to give 5-phenylsalicylaldehyde (5A) as yellow crystals, mp: 98°–99° C.

12.2 g of acetyl chloride was added to a mixture of 10.3 g of 5A, and 120 ml of carbon disulfide, then 21.8 g of anhydrous aluminum chloride was added in portions to the stirred mixture. The mixture then was stirred at room temperature for 2.5 hours, the temperature rising to 32° C. The mixture was poured into 1 liter of ice water and stirred for 30 minutes, and the solution was extracted with ether. The extract was dried (MgSO₄) and concentrated. The residue was washed with ether and dissolved in 100 ml of chloroform. The solution was treated with activated charcoal and 100 ml of hexane was added. The resulting solution was concentrated to about 100 ml and cooled to give 5, mp: 105°–107° C.

EXAMPLE 6—Ethyl 5-(4-acetyloxyphenyl)benzofuran-2-carboxylate (6)

2 ml of trifluoroacetic acid was added to a mixture of 30.8 g of 5 and 500 ml of acetic acid, then 100 ml of 30% hydrogen peroxide solution was added drop-by-drop. The mixture was stirred over a weekend at room temperature, then heated at 55°–60° C. for 8 hours and allowed to stand overnight. The resulting solid was collected, dried under reduced pressure, recrystallized from a 2/3 v/v methylene chloride/hexane mixture to give 6, mp: 143°–145° C.

EXAMPLE 7—Ethyl 5-(4-(1-hydroxyethyl)phenyl)benzofuran-2-carboxylate (7)

1.2 g of sodium borohydride was added in one portion to a stirred mixture of 15.0 g of 5, 200 ml of ether and 40 ml of ethanol. The mixture was stirred at room temperature for 2 hours. The solvents were evaporated under reduced pressure. 1.6 liters of water was added to the residue and the mixture was extracted with chloroform. The extract was dried (MgSO₄) and the solvent was evaporated under reduced pressure. The residue was dissolved in 150 ml of chloroform. The solution was filtered through charcoal. 400 ml of hexane was added to the filtrate and the solid which formed was collected, recrystallized from a 3/50 v/v mixture of chloroform and hexane and dried in a vacuum oven to give 7, mp: 108°–109° C.

EXAMPLE 8—Ethyl 5-(4-(acetylamino)phenyl)furan-2-carboxylate (8)

A mixture of 6.2 g of 5, 100 ml of ethanol and 200 ml of tetrahydrofuran was heated to 60°–70° C. A solution of 1.53 g of hydroxylamine hydrochloride and 1.16 g of sodium carbonate in 20 ml of water was added. The mixture was heated for 3 hours at 60°–70° C. The resulting solid was collected, washed with water, then ethanol, and extracted with methylene chloride. The solvent was evaporated from the extract under reduced pressure to give ethyl 5-(4-(1-(hydroxyimino)ethyl)phenyl-2-benzofurancarboxylate (8A), mp: 220°–222° C.

56.5 g of phosphorus pentachloride was added in portions to a solution of 55.0 g of 8A in 1 liter of chloroform, and the mixture was stirred at room temperature for 16 hours. The solvent was evaporated under reduced pressure. The residue was suspended in 4 liters of water, the mixture was stirred vigorously for 30 minutes and filtered. The solid was extracted with chloroform. The extract was washed, successively, with water, saturated sodium bicarbonate solution, and water, then was filtered through celite (to break the emulsion). The filtrate was dried (MgSO₄) and the solvent was evaporated under reduced pressure. The residue was triturated with ether. The ether phase was separated, then concentrated to about half its volume under reduced pressure and allowed to stand over a weekend. The solid which formed was collected and dissolved in 400 ml of chloroform. The solution was filtered over charcoal and diluted with 400 ml of hexane. The resulting solid was collected and dry column chromatographed over silica gel, using a 1/9 v/v mixture of tetrahydrofuran and chloroform as eluent. After removal of the solvents, the appropriate fractions were combined and extracted with tetrahydrofuran. The solvent was evaporated under reduced pressure, and the residue was triturated with ether. The resulting solid was collected and dried under reduced pressure to give 8, mp: 174°–176° C.

EXAMPLE 9—Ethyl 5-(4-aminophenyl)benzofuran-2-carboxylate (9)

A mixture of 3.0 g of 8, 50 ml of 6 N hydrochloric acid and 50 ml of ethanol was stirred and refluxed for 5 hours. The solution was concentrated to half its volume, the resulting solid was collected and dissolved in chloroform containing some triethylamine. The solution was washed with water, dried (MgSO₄) and filtered. The solvent was evaporated from the filtrate under reduced pressure. The residue was dry column chromatographed using a 1/9 v/v tetrahydrofuran/chloroform mixture as eluent. The solvents were evaporated, the appropriate fractions were combined and extracted with chloroform. The extract was filtered and the solvent was evaporated under reduced pressure. The residue was refluxed in petroleum ether for 8 hours. The mixture was filtered and the filtrate was held in a freezer overnight. The resulting solid was collected and dried to give 9, mp: 95°–97° C.

EXAMPLE 10—Ethyl 2,3-dihydro-5-phenylbenzofuran-2-carboxylate (10)

A mixture of 0.99 g of 5A, 0.96 g of diethyl bromomalonate and 1.25 g of anhydrous potassium carbonate in 20 ml of 2-butanone, was refluxed for 10 hours. The solvent was evaporated under reduced pressure. The residue was cooled, mixed with 100 ml of water and extracted with ether. The extract was washed with cold 5% sodium hydroxide solution and water and then concentrated under reduced pressure. The residue was recrystallized from ethanol to give ethyl 5-phenylbenzofuran-2-carboxylate (10B), as white crystals, mp: 109°–110° C.

A mixture of 1.3 g of 10B and 50 ml of 10% alcoholic potassium hydroxide was refluxed for 4 hours. The solvent was evaporated under reduced pressure and the residue was washed with ether and dissolved in water. The basic solution was acidified with dilute hydrochloric acid and extracted with ether. The ether layer was extracted with dilute sodium bicarbonate solution. The aqueous extract was acidified with dilute hydrochloric acid and extracted with ether. The ether extract was dried ($Na_2SO_4$), concentrated under reduced pressure, and the resulting residue was crystallized from ethanol to give 5-phenyl-2-benzofurancarboxylic acid (10C), as white solid, mp: 220°–221° C.

5.0 g of 10C was mixed with 90 ml of 10% sodium hydroxide solution. Sodium amalgam (prepared from 1.5 g of sodium and 50 g of mercury) was added to the stirred mixture over a period of one hour. The mixture was then stirred for 24 hours and allowed to stand at room temperature for an additional 24 hours. The mercury was separated, and he solution was neutralized with dilute hydrochloric acid and extracted with ether. The extract was dried ($Na_2SO_4$), concentrated under reduced pressure, and the residue was recrystallized from ethanol to give 2,3-dihydro-5-phenyl-2-benzofurancarboxylic acid (10D), as white crystals, mp: 186°–187° C.

A mixture of 2.5 g of 10D, 60 ml of ethanol, 20 ml of dry benzene and 2 ml of concentrated sulfuric acid was refluxed for seven hours, with removal of water as it formed. The resulting mixture was concentrated, and the residue was dissolved in ether. The solution was washed with saturated sodium bicarbonate solution and water. The aqueous phase was separated and extracted with ether. The combined organic layers were dried ($Na_2SO_4$) and the solvent was evaporated under reduced pressure. The residue was distilled to give 10, as a colorless liquid, bp: 180°–181° C., 0.35 Torr.

EXAMPLES 11-17

By procedures similar to those described in Example 10, the following further individual species of the 2,3-dihydro subclass of the class of Formula I were prepared from the corresponding individual species of the furan subclass:

| Example No. | Compound No. | X | R | m.p. (°C.) |
|---|---|---|---|---|
| 11 | 11 | 5-benzyl | ethyl | 47.5–48.5 |
| 12 | 12 | " | allyl | 26–27 |
| 13 | 13 | 4-phenoxy | ethyl | 56–58 |
| 14 | 14 | 5-(4-(1-hydroxyethyl)phenyl) | methyl | 98–100 |
| 15 | 15 | 5-(4-acetamidophenyl) | ethyl | 164–166 |
| 16 | 16 | 5-cyclohexyl | ethyl | 50–52 |
| 17 | 17 | 6-phenoxy | " | (liquid) |

EXAMPLE 18—Ethyl 2,3-dihydro-5-(4-chlorophenyl)benzofuran-2-carboxylate (18)

A solution of 6.9 g of sodium nitrite in 40 ml of water was added drop-by-drop to a stirred mixture of 30 g of 9 and 160 ml of 6 N hydrochloric acid, the rate of addition being adjusted to maintain the temperature of the reaction mixture at 0°–5° C. The mixture was stirred for 1 hour at 0°–5° C., then added, with vigorous stirring to 50 ml of 20% aqueous cuprous chloride heated to 70° C. The resulting mixture was heated to 70° C., then allowed to cool. The solid was collected, washed with water, dried ($P_2O_5$, reduced pressure) and dissolved in tetrahydrofuran. The solution was suspended on 75 g of silica gel and dry column chromatographed, using chloroform as eluent. The product was removed from the combined appropriate fractions with tetrahydrofuran. The solvent was evaporated and the residue was dried (drying pistol, $P_2O_5$, refluxing acetone) to give ethyl 5-(4-chlorophenyl)benzofuran-2-carboxylate (18A), mp: 108°–110° C.

61.5 g of 2.5% sodium amalgam was added in portions to a mixture of 6.7 g of 18A, 270 ml of tetrahydrofuran and 90 ml of ethanol. The mixture was stirred for 20 hours at room temperature. The solvent was evaporated under reduced pressure. The residue was dissolved in 1 liter of hot water containing 4 ml of saturated sodium hydroxide solution. The mixture was filtered, the filtrate was cooled with an ice bath, and acidified to pH=2. The mixture was stirred for 30 minutes, the resulting solid was collected, washed with water and dried (reduced pressure, $P_2O_5$, refluxing acetone) to give 2,3-dihydro-5-(4-chlorophenyl)-2-benzofurancarboxylic acid (18B), mp: 147°–149° C.

3.3 g of 18B, 300 ml of ethanol and 0.5 ml of concentrated sulfuric acid were mixed, and the stirred mixture was refluxed through a Soxhlet extractor containing 3A molecular sieve for 5 hours. The solvent was evaporated under reduced pressure and the residue was suspended in chloroform. The suspension was washed with saturated sodium bicarbonate solution, dried ($MgSO_4$) and filtered. The solvent was evaporated from the filtrate under reduced pressure and the residue was wet column chromatographed using toluene as eluent. The appropriate fractions were combined, the solvent was evaporated under reduced pressure and the residue was triturated with a small amount of petroleum ether. The solid product was collected, dried under reduced pressure over $P_2O_5$, then crystallized and recrystallized from ether to give 18, mp: 94°–96° C.

Compounds of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the uptake of the radioactive carbon by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half of the normal calcium ion concentration, 60 micromoles of glucose, 0.5 micro-Curie of glucose-$U^{14}C$, and 300 microunits of insulin, and 5% dimethyl sulfoxide (DMSO). The test compound was added as a solution or suspension in DMSO and was present as a concentration of 100 micrograms per milliliter of incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound. The data obtained are reported as the percent inhibition of lipogenesis compared to the results obtained in the control tests wherein only the test compound was omitted. The results are summarized in Table I.

Table I

| Compound | Percent Inhibition |
|----------|--------------------|
| 1 | 45 |
| 2 | 23 |
| 3 | 47 |
| 4 | 28 |
| 5 | 24 |
| 6 | 56 |
| 7 | 71 |
| 8 | 52 |
| 9 | 45 |
| 10 | 21 |
| 11 | 40 |
| 12 | 36 |
| 13 | 20 |
| 14 | 85 |
| 15 | 88 |
| 16 | 21 |
| 17 | 29 |
| 18 | 28 |

Compounds of Formula I can be used to inhibit lipogenesis in mammals such as, for example, pets, animals in zoo, livestock, fur-bearing animals and domestic animals, including, but not limited to dogs, cats, mink, sheep, swine, cattle, horses, mules and donkeys. The effect is obtained by administering an effective amount of one or a mixture of the inhibitors orally or parentally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the inhibitor needed to inhibit lipogenesis will depend upon the particular compound(s) used, and the particular animal being treated. However, in general, satisfactory results are obtained when the inhibitor is administered in a dosage of from about 1 to about 500 milligrams per kilogram of the animal's body weight. The inhibitor can be administered in a single dose or in a series of doses in the same day, or over a period of days. For any particular animal, a specified dosage regimen should be adjusted according to the individual need, the particular inhibitor used, and the professional judgement of the person administering or supervising the administration of the inhibitor. It is to be understood that the dosages set forth herein are exemplary only, and that they do not, to any extent, limit the scope or practice or the invention.

The invention claimed is:

1. A method of inhibiting lipogenesis in a mammal, which comprises administering to a mammal, orally or parenterally, an effective amount of a compound of the formula

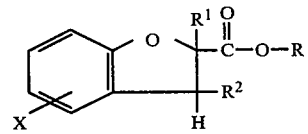

wherein R is alkyl of from one to four carbon atoms or is 2-propenyl, (a) $R^1$ and $R^2$ together represent a second bond between the two carbon atoms, and X is one of the following moieties, bonded to the carbon atom in the indicated position on the molecule:
(1) 5-benzyl;
(2) 5-(alkyloxy of from three to six carbon atoms;
(3) 4-phenoxy;
(4) 5-benzoyl;
5-(4-acetylphenyl);
(6) 5-(4-(acetyloxy)phenyl);
(7) 5-(4-(1-hydroxyethyl)phenyl);
(8) 5-(4-acetamidophenyl);
(9) 5-(4-aminophenyl);
or
(b) $R^1$ and $R^2$ each represents a hydrogen atom, and X is one of the following moieties, bonded to the carbon atom in the indicated position on the molecule:
(1) 5-phenyl;
(2) 5-cyclohexyl;
(3) 5-benzyl;
(4) 6-phenoxy;
(5) 4-phenoxy;
(6) 5-(4(1-hydroxyethyl)phenyl);
(7) 5-(4-chlorophenyl);
(8) 5-(4-acetamidophenyl).

* * * * *